United States Patent [19]

Gandilhon

[11] 4,138,411
[45] Feb. 6, 1979

[54] PROCESS FOR THE ISOMERIZATION OF AROMATIC ALKENYL COMPOUNDS

[75] Inventor: Pierre Gandilhon, Quartier Bas-Rivoire a Charly, France

[73] Assignee: Rhone-Poulenc S. A., Paris, France

[21] Appl. No.: 676,676

[22] Filed: Apr. 14, 1976

Related U.S. Application Data

[63] Continuation of Ser. No. 843,173, Jul. 18, 1969, abandoned.

[30] Foreign Application Priority Data

Jul. 19, 1968 [FR] France .............................. 68.159950
Feb. 19, 1969 [FR] France .............................. 69.690418

[51] Int. Cl.$^2$ .................... C07D 317/44; C07C 43/20; C07C 15/00; C07C 39/02
[52] U.S. Cl. ............................ 260/340.5 R; 260/577; 260/668 A; 568/627; 568/656; 568/649; 568/783; 568/657; 568/658; 568/650; 568/763; 568/765; 568/716; 568/651; 568/652; 568/654; 568/766; 568/774
[58] Field of Search ............ 260/340.5, 668 A, 683.2, 260/612 D, 621 E, 613 D, 577, 340.5 R; 568/783

[56] References Cited

U.S. PATENT DOCUMENTS

| | | | |
|---|---|---|---|
| 2,002,447 | 5/1935 | Deichsel | 260/621 E |
| 2,666,771 | 1/1954 | Zettlemoyer et al. | 260/613 D |
| 2,682,474 | 6/1954 | Bell et al. | 260/613 D |
| 2,804,489 | 8/1957 | Pines et al. | 260/668 A X |
| 3,205,282 | 9/1965 | Sparke et al. | 260/683.2 X |
| 3,257,415 | 6/1966 | O'Grady et al. | 260/340.5 R |
| 3,367,988 | 2/1968 | McEuen | 260/683.2 |
| 3,697,580 | 10/1972 | Overwien et al. | 260/612 D |
| 3,852,305 | 12/1974 | Nagase et al. | 260/613 D |

FOREIGN PATENT DOCUMENTS

| | | | |
|---|---|---|---|
| 550405 | 12/1957 | Canada | 260/621 E |
| 2032135 | 11/1970 | France | 260/577 |
| 981694 | 1/1965 | United Kingdom | 260/683.2 |
| 1205740 | 9/1970 | United Kingdom | 260/340.5 R |

OTHER PUBLICATIONS

Bond et al, Trans. Faraday Soc. 64, II pp. 3077–3085 (1968).

*Primary Examiner*—Ethel G. Love
*Attorney, Agent, or Firm*—Cushman, Darby & Cushman

[57] ABSTRACT

Aromatic alkenyl compounds, for example, eugenol and safrole, are isomerized, for example to isoeugenol and isosafrole, by contact with a ruthenium or osmium catalyst.

8 Claims, No Drawings

PROCESS FOR THE ISOMERIZATION OF AROMATIC ALKENYL COMPOUNDS

This is a continuation of application Ser. No. 843,173 filed July 18, 1969, now abandoned.

The present invention relates to a process for the isomerization of aromatic alkenyl compounds.

It is often desirable to be able to isomerize aromatic compounds containing alkenyl groups, for example a more readily accessible compound into a less readily accessible, but more valuable, compound. Examples of such isomerizations are the conversion of eugenol (2-methoxy-4-allylphenol) into isoeugenol (2-methoxy-4-propenylphenol) and of safrole (3,4-methylenedioxy-alkylbenzene) into isosafrole (3,4-methylenedioxy-propenylbenzene).

The alkaline bases are the isomerization catalysts most used for causing isomerizations of this kind. However, in this method it is necessary to use large quantities of the alkaline bases, such as caustic soda or caustic potash and generally the weight of alkaline base is equal to the weight of the compound being isomerized.

It has now been found that ruthenium and osmium are effective catalysts in very small amount for the isomerization of aromatic compounds containing alkenyl groups.

The present invention therefore provides a process for the isomerization of an aromatic alkenyl compound of the formula:

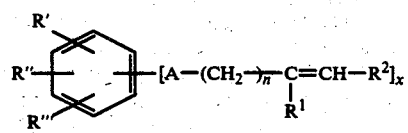

in which R', R" and R"', which are the same or different, each represent hydrogen, alkyl (preferably of up to 5 carbon atoms), alkoxy (preferably of up to 5 carbon atoms) halogen amino, hydroxy or a radical of formula:

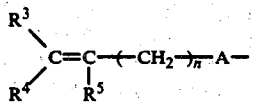

(in which $R^3$ and $R^4$ are each alkyl of 1 to 5 carbon atoms and $R^5$ is hydrogen or methyl) and two of the radicals R', R" and R"' carried by two adjacent carbon atoms of the aromatic ring can be joined together to form a divalent radical, for example a radical —O—CH$_2$—O—, n is an integer from 1 to 10, A is a valence bond, an oxygen atom or a —NR$^6$— group (where $R^6$ is hydrogen or alkyl of 1 to 5 carbon atoms). $R^1$ and $R^2$ are the same or different and represent hydrogen or alkyl of 1 to 5 carbon atoms, and x is an integer from 1 to 3, which comprises contacting the said compound with a ruthenium or osmium catalyst.

The product of the isomerization is in general one in which the double bond is shifted nearer to the benzene ring. Thus the first product can be represented by the formula:

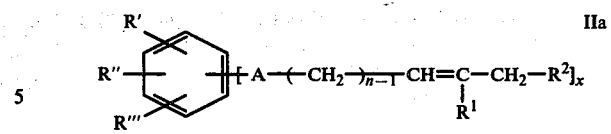

wherein the various symbols are as hereinbefore defined. Where n is greater than one, such a product can be further isomerized to a compound of formula:

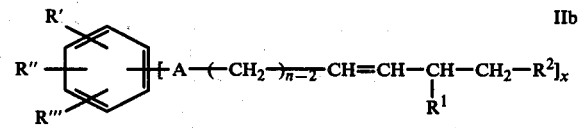

and so on until a compound of the formula:

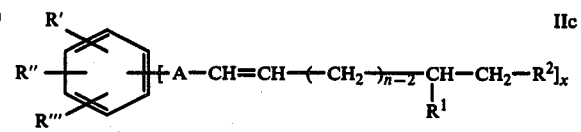

is reached which cannot be further isomerized.

By way of example R', R" and R"' can each represent chlorine, methyl, ethyl, propyl, butyl, amyl, methoxy, ethoxy, propoxy, butoxy, 3-methyl-2-butenyl, or 3-methyl-2-butenyloxyl and $R^1$ and $R^2$ can each represent methyl, ethyl, propyl, butyl or amyl.

Examples of aromatic alkenyl hydrocarbons of formula I in which A represents a valence bond, are: allylbenzene; 4-phenyl-1-butene; 4-phenyl-2-butene; 5-phenyl-1-pentene; 5-phenyl-2-pentene; 1-phenyl-2-pentene; 2-methyl-4-phenyl-1-butene; 6-phenyl-1-hexene; otho-, meta- and para-allyltoluene and p-diallylbenzene. Examples of alkenyl phenols and their derivatives of formula I are o-, m- and p-allylphenol; 2,6-diallylphenol; 2-allyl-3,5-dimethylphenol; 2,6-diallyl-4-(2-butenyl)-phenol; 2-(3-butenyl)phenol; 2-allyl-6-ethoxyphenol-(o-allylethacol); 2-methoxy-4-allylphenol (eugenol) and 2,6-dimethoxy-4-allylphenol. Other compounds of formula I are phenol ethers, for example allyloxybenzene; 4-phenoxy-1-butene; 3,4-dimethoxyallylbenzene (methyleugenol); safrole (1-allyl-3,4-methylenedioxybenzene); 2,4,6-trimethoxyallylbenzene; and 3-methyl-4-(2-butenyloxy)allylbenzene.

The ruthenium catalyst which can be used in the process of the invention may be, for example, a halide, thiocyanate or salt of an oxygen-containing mineral acid, such as a sulphate, nitrate, oxy-halide or hydroxyhalide or a salt of an aliphatic, cycloaliphatic or aromatic organic acid, such as the acetate, oxalate, stearate, or naphthenates. The alcoholates and phenates can also be used. Other inorganic and organic ruthenium compounds which can be used are the alkali and alkaline earth metal ruthenates, mixed salts of ruthenium and alkali metals, such as the sodium or potassium haloruthenates and halogen, nitrosyl or amino derivatives, such as nitrosochlororuthenium or trichlororuthenium hexamine. Chelate compounds, such as the acetylacetonates, optionally substituted, for example, by aliphatic or cycloaliphatic groups, or by halogen atoms, such as 3-bromo-2,4-pentadionatoruthenium-(III) or 1,1,1-trifluoro-2,4-pentadionatoruthenium(III), the glyoximates, quinoleinates, salicylaldehydates and the derivatives of ethylene diamine, o,o'-dipyridyl and o- phenanthroline, are also suitable. Ruthenium compounds derived from tris(β-dionato)ruthenium are also suitable. Thus, it is in particular possible to employ the complexes of the formula:

$$(Diket)_2 (CO)Ru\ L \qquad\qquad III$$

in which (Diket) represents a β-diketone radical and L represents a monodentate or polydentate ligand other than a β-diketone. These complexes and the processes for the preparation thereof have been described in French Pat. No. 1,526,197. Among these complexes, it is possible particularly to mention bis-(acetylacetonato)-carbonylacetonitrile ruthenium; bis-(acetylacetonato)-carbonylpropionitrile ruthenium; bis-(acetylacetonato)-carbonylacrylonitrile ruthenium and bis-(acetylacetonato)carbonylpyridyl ruthenium.

It is also possible to use complexes of the general formula:

$$[(Diket)_2 (CO)\ Ru]_2 \qquad\qquad IV$$

in which (Diket) has the meaning given above, obtained by reaction of a tris-(β-dionato)ruthenium with a compound which is a carbonyl group donor (particularly alcohol), for example the compound of formula:

$$[(C_5H_7O_2)_2 (CO)\ Ru]_2 \qquad\qquad V$$

Complexes of the formula:

$$(Diket)_2\ Ru\ L_2$$

in which (Diket) and L have the meaning previously given, can also be used as isomerization catalysts in the process of the invention. These compounds can be prepared either by the action of a ligand L or a tris-(β-dionato)ruthenium in a hydrogen atmosphere in the presence of a hydrogenation catalyst, or by substitution in the complex of formula V of the ligand L by another ligand L having a higher power as a donor of electrons. Examples of complexes of formula V are bis-(acetylacetonato)-bis-(acetonitrile)-ruthenium; bis-(acetylacetonato)-bis-(propionitrile)-ruthenium; bis-(acetylacetonato)-bis-(pyridyl)ruthenium; bis-(acetylacetonato)bipyridyl ruthenium and bis-(acetylacetonato)phenanthroline ruthenium.

Another particularly suitable class of catalysts are the complexes formed by ruthenium derivatives with electron donors. Such complexes are for example obtained by using, as ruthenium derivatives, halogen derivatives, and carbonyl derivatives, such as the trimer of ruthenium tetracarbonyl, or ruthenium nitrosyls and as electron donors, substances with pairs of isolated electrons, such as phosphines, arsines, stibines, amines or substances capable of forming structures with pairs of isolated electrons, which are thus also capable of acting as electron donors. In particular, it is possible to use the complexes formed with the electron donors specifically mentioned in Franch Pat. No. 1,337,558. Particularly suitable, therefore, are complexes originating from the reaction of the ruthenium compounds, particularly the halides and the hydridohalides, with aliphatic or cycloaliphatic monoolefines and diolefines, as for example butadiene, isoprene, cyclooctadiene, with activated olefines, such as the acrylic or methacrylic derivatives, namely, acrolein, methacrolein, acrylamide, with the saturated or unsaturated aliphatic, cycloaliphatic or aromatic nitriles, e.g. acetonitrile, propionitrile, acrylonitrile, methacrylonitrile, cyanocyclohexane, benzonitrile, toluonitrile, with the saturated or unsaturated dinitriles, such as malonitrile, succinonitrile, adiponitrile, dicyanobutanes, dicyanocyclobutanes and dicyanobutenes, and aliphatic or aromatic isonitriles.

Such complexes can be prepared by heating a ruthenium halide with an agent which is an electron donor, possibly in the presence of a solvent which can itself participate in the preparation of the complex.

Among these complexes, it is in particular possible to use those which are described in French Pat. No. 1,505,334 and its Addition No. 91,167, such as dichlorotetrakis(acrylonitrile)ruthenium; dichlorotetrakis(methacrylonitrile)ruthenium; dichlorotetrakis(benzonitrile)ruthenium; dichloro-tris-(acetonitrile)ruthenium; trichloro-tris(propionitrile)ruthenium and the complexes of formula:

$$Ru_2Cl_6[NC-CH_2)_4CN]_3;$$
$$RuCl_3[NC-CH_2CH_2-CH=CH-CN]_2;$$
$$Ru_2Cl_4[NC-CH_2CH_2-CN]_3.$$

Suitable osmium catalysts for use in the present invention are the halides (for example osmium trichloride), mineral acid salts such as the sulphates and nitrates; and organic acid salts such as the acetates, oxalates, stearates and naphthenates. It is also possible to employ the complexes of osmium with monodentate or polydentate ligands, such as tetracarbonyl-bis-(cyclopentadienyl)diosmium, bis-(cyclopentadienyl)osmium and mixed salts of osmium and alkali metals, such as the sodium or potassium hexachloroosmiates or bromoosmiates.

The quantity of catalyst used in the new process corresponds in general to a quantity of elementary osmium or ruthenium which is from 0.0001% to 2% by weight of the compound to be isomerized. The catalyst can be used in the solid or finely divided state, with or without a support, in solution in the compound subjected to the isomerization, or in an appropriate solvent. The catalyst can be re-used, after separation, in a new operation.

The aromatic alkenyl compounds of formula I can be isomerized in the presence or absence of a solvent, such as water, or an organic compound, such as a saturated aliphatic hydrocarbon, saturated cycloaliphatic hydrocarbon (cyclohexane), aromatic hydrocarbon (benzene, toluene, or xylene), ether (diethyl ether or dioxan) or an alcohol (methanol, ethanol, butanol or ethylene glycol).

The temperature of the reaction depends on the compound subjected to the isomerization and on the catalyst used, but it is generally from 40° to 200° C.

The ruthenium or osmium compounds used as isomerization catalysts for the aromatic alkenyl compounds generally permit a rapid reaction at relatively low temperatures. More particularly, they permit the isomerization of allylphenols, such as eugenol, methyleugenol or allylphenol, and of allylphenol derivatives, such as safrole, at temperatures which are below 150° C., with contact times which are from approximately 10 minutes to 6 hours, leading in the majority of cases to conversion rates of the product to be isomerized and to yields of isomer products (propenyl phenols and derivatives) which are between 90 and 100%. In the case of compounds capable of leading to isomers differing in the position of the ethylenic double bond, such as aromatic compounds with alkenyl groups comprising more than 3 carbon atoms, the catalysts used in the invention make it possible to obtain a selective migration of the double bond, by selecting the conditions of the reaction (nature of catalyst, reaction temperature).

The following Examples illustrate the present invention.

EXAMPLE 1

100 g. of eugenol (2-methoxy-4-allylphenol) and 0.2 g. of ruthenium acetylacetonate (i.e. 0.005% of elementary ruthenium) are placed in a 2-liter spherical flask equipped with a thermometer, a stirrer system and a reflux condenser, and the contents of the flask are heated to 130° C. for 4 hours 20 minutes. The reaction mass is distilled. 988 g. of product are recovered, containing 99.4% of isoeugenol (2-methoxy-4-propenylphenol) measured by gas-liquid chromatography.

The conversion rate of the eugenol is 99.4% and the yield of isoeugenol with respect to the converted eugenol is 98.8%.

EXAMPLE 2

A mixture of 200 g. of eugenol and 10 mg. of $Ru_3(CO)_{12}$ (i.e. 0.0023% of elementary ruthenium) is heated to 130° C. for 1 hour 55 minutes. By distilling the reaction mass, 198 g. of isoeugenol are recovered. The yield based on the eugenol used is 99% (conversion rate 100%).

EXAMPLE 3

A mixture of 5 g. of eugenol, 25 cc. of benzene and 50 mg. of different ruthenium complexes is heated to 85° C. for 6 hours. After distillation and measurement by gas-liquid chromatography, the results set out in Table I are obtained:

TABLE I

| Catalysts | Conversion rate | Yield of isoeugenol with respect to converted eugenol |
|---|---|---|
| $(C_5H_7O_2)_2 Ru(CH_3-CN)_2$ | 100% | 97% |
| $[(C_5H_7O_2)_2 Ru(CO)]_2$ | 98% | 91% |
| $(C_5H_7O_2)_2 Ru(CO)(CH_3-CH_2-CN)$ | 95% | 90% |
| $(C_5H_7O_2)_2 Ru(CO)(CH_3-CN)$ | 100% | 94% |

EXAMPLE 4

5 g. of eugenol are isomerized using 50 mg. of $Ru_3(CO)_{12}$ (i.e. 0.48% of elementary ruthenium) under the conditions and with the results indicated in Table II.

TABLE II

| Solvent Nature | Solvent Volume | Temperature in °C. | Duration | Conversion rate | Yield of isoeugenol with respect to the converted eugenol |
|---|---|---|---|---|---|
| Toluene | 25 cc. | 115° C. | 6 h. | 99.1% | 92% |
| Benzene | — | 85° C. | — | 100% | 96% |
| Cyclohexane | — | — | — | 100% | 96% |
| Ethanol | — | 78° C. | — | 100% | 90% |
| Dioxane | — | 85° C. | — | 99% | 96% |

EXAMPLE 5

Operating as in Example 1, the isomerization of methyl-eugenol (3,4-dimethoxyallylbenzene) into isomethyl-eugenol (3,4-dimethoxy-1-propenylbenzene) is carried out under the following conditions and with the following yields:

TABLE III

| Methyl eugenol in g. | Catalyst nature | Catalyst weight in mg. | Duration | Temperature in °C | Conversion rate | Yield of iso ethyl eugenol with respect to the converted methyl eugenol |
|---|---|---|---|---|---|---|
| 10 | $Ru_3(CO)_{12}$ | 10 | 10 min | 115 | 98.7% | 98.6% |
| 30 | — | 3 | 35 min | — | 100% | 98.3% |
| 10 | $(C_5H_7O_2)_3Ru$ | 10 | 1 h. 15 min. | — | 99.3% | 97% |
| 20 | $RuCl_3-\beta^{(1)}$ | 150 | 4 h. 25 min. | 130 | 96% | 94% |

(1) The $\beta$-form of the ruthenium trichloride was prepared by the method of HYDE et al., J. of LESS COMMON METALS 8, 428–434 (1965); it does not contain the $\alpha$ form.

EXAMPLE 6

50 g. of safrole are isomerized into isosafrole (1-propenyl-3,4-methylenedioxybenzene) under the following conditions and with the following results:

TABLE IV

| Catalysts Nature | Weight in mg. | Duration | Temperature in °C. | Conversion rate | Yield of isosafrole with respect to the converted safrole |
|---|---|---|---|---|---|
| $Ru_3(CO)_{12}$ | 5 | 3 h. 30 | 115 | 98% | 99% |
| $(C_5H_7O_2)_3Ru$ | 20 | — | 130 | 95% | 99.2% |
| $RuCl_3-\beta$ | 200 | 3 h. 05 | — | 100% | 98.4% |

EXAMPLE 7

A mixture of 10 g. of o-allylphenol and 0.01 g. of ruthenium acetylacetonate is heated to 115° C. for 1½ hours. After distillation, 8.55 g. of a mixture are recovered, in which there are found by gas-liquid chromatography 12.7% of o-allylphenol and 87.3% of o-propenylphenol. The conversion rate is 89% and the yield of o-propenylphenol with respect to the converted o-allylphenol is 84%.

EXAMPLE 8

A mixture of 10 g. of allyloxybenzene and 0.1 g. of ruthenium acetylacetonate is brought to 140° C. for 6 hours. After distillation, 9.2 g. of a product containing only propenyloxybenzene are obtained. The yield of propenyloxybenzene is 92% based on the converted allyloxybenzene.

EXAMPLE 9

A mixture of 10 g. of allyloxybenzene and 0.05 g. of ruthenium tetracarbonyl trimer is brought to 115° C. for 6 hours. After the usual treatments of the reaction mass, it is found that the conversion rate of the allyloxybenzene is 100% and the yield of propenyloxybenzene based on the converted allyloxybenzene is 93%.

EXAMPLE 10

A mixture of 5 g. of allylbenzene and 50 mg. of $Ru_3(CO)_{12}$ is brought to 105° C. for 1 hour. The conversion rate of the allylbenzene is 92% and the yield of propenylbenzene based on the converted allylbenzene is 87%.

EXAMPLE 11

5 g. of allylbenzene, 25 cc. of dioxane and 50 mg. of ruthenium acetylacetonate are refluxed at 105° C. for 1 hour. The conversion rate of the allylbenzene is 98% and the yield of propenylbenzene based on the converted allylbenzene is 88%.

EXAMPLE 12

10 g. of 4-phenyl-1-butene are treated under the conditions and with the results set out in the following Table:

TABLE V

| Catalyst | | | Temperature in °C | Conversion rate | Yields based on converted 4-phenyl-1-butene | |
|---|---|---|---|---|---|---|
| Nature | Weight | Duration | | | of 1-phenyl-2-butene | of 1-phenyl-1-butene |
| $RuCl_3$-β | 50 mg | 4 h. | 130 | 100% | 15% | 74% |
| Ruthenium acetylacetonate | 10 mg | 4 h. 30 min. | — | 98% | 43% | 51% |
| $Ru_3(CO)_{12}$ | 10 mg | 2 h. 15 min. | — | 99% | 17% | 77% |

EXAMPLE 13

The procedure of Example 12 is followed, but varying the temperature and the duration of the reaction in order to regulate the conversion rate of the 4-phenyl-1-butene. The catalyst is ruthenium acetylacetonate. The following results are obtained:

TABLE VI

| Temperature in °C | Duration | Conversion rate | Yield based on converted 4-phenyl-1-butene | |
|---|---|---|---|---|
| | | | of 1-phenyl-2-butene | of 1-phenyl-1-butene |
| 100° C. | 3 h. 35 | 69.6% | 83.5% | 5.3% |
| 115° C. | 1 h. 30 | 78.5% | 87% | 6.8% |
| — | 50 min. | 52% | 88.5% | 2% |

EXAMPLE 14

A mixture of 2 g. of 4-phenoxy-1-butene and 4 mg. of $Ru_3(CO)_{12}$ is heated for 6 hours at 130° C. After treatment of the reaction mass, there is found an isomerization of 75% of the 4-phenoxy-1-butene into 1-phenoxy-2-butene and 1-phenoxy-1-butene with yields of 82.6% and 17.3%, relatively to the transformed 4-phenoxy-1-butene.

EXAMPLE 15

A mixture of 50 g. of safrole and 0.038 g. of osmium trichloride is brought for 10 minutes to 135° C. After distillation, 46 g. of a mixture, containing (as measured by gas-liquid chromatography) 2.7% of safrole, 8 % of cis-isosafrole and 89.3% of trans-isosafrole, are obtained. The conversion rate if 97.5% and the yield is 90%, based on the converted safrole.

EXAMPLE 16

A mixture of 73 g. of eugenol and 5.7 mg. of osmium trichloride is brought for 4 hours 25 minutes to 130° C. After distillation, 65.2 g. of a mixture, containing (as measured by gas-liquid chromatography) 13.8% of eugenol, 6.8% of cis-isoeugenol and 79.4% of trans-isoeugenol are obtained. The conversion rate is 88% and the yield is 85.2%, based on the converted eugenol.

EXAMPLE 17

A mixture of 13 g. of o-allylphenol and 0.006 g. of osmium trichloride is brought for 7 3/4 hours to 130° C. After distillation, 10 g. of a mixture composed of 18.7% of o-allylphenol, 33.1% of cis-orthopropenylphenol and 48.2 % of trans-orthopropenylphenol are obtained. The conversion rate is 86% and the yield is 70.5%, based on the converted o-allylphenol.

EXAMPLE 18

A mixture of 20 g. of crude clove oil containing about 80% of eugenol and 50 mg. of osmium trichloride is heated for 4¼ hours to 135° C. After distillation, a fraction weighing 13.3 g. and containing, (as determined by gas-liquid chromatography) 5.5% of cis-isoeugenol and 94.5% of trans-isoeugenol is obtained. The yield is 83%, based on the eugenol originally present in the clove oil.

EXAMPLE 19

A mixture of 5 g. of p-allylcumene and 5 mg. of osmium trichloride is brought to 110° C. for 7¼ hours. After distillation, a fraction weighing 4.2 g. containing (as measured by gas-liquid chromatography) 31% of p-allylcumene, 12% of cis-p-propenylcumene and 57% of trans-p-propenylcumene is obtained. The conversion rate is 74% and the yield is 78.5%, based on the converted p-allylcumene.

EXAMPLES 20 TO 41

Various other compounds of formula I were treated in accordance with this invention in the manner and with the results indicated in the following Table.

TABLE VII

| Ex. | Compound of formula I — Nature | Quantity in g. | Catalyst — Nature | Quantity in mg. | Duration | Temperature in °C. | Degree of conversion in % | Product of isomerisation — Nature | Yield based on converted starting material in % |
|---|---|---|---|---|---|---|---|---|---|
| 20 | Methallylbenzene (a) | 5 | $Ru_3(CO)_{12}$ | 25 | 1h45 | 130 | 92.6 | Isobutenylbenzene (b) | 83 |
| 21 | Methallylbenzene (a) | 10 | $(C_5H_7O_2)_2Ru(CH_3—CH)_2$ | 10 | 5h45 | 150 | 91 | Isobutenylbenzene (b) | 90 |
| 22 | p-allylcumene | 30.5 | $(C_5H_7O_2)_2Ru(CH_3—CH)_2$ | 30.5 | 3h35 | 130 | 95.5 | p-propenylcumene | 94 |
| 23 | p-allylcumene | 8.8 | $Ru_3(CO)_{12}$ | 4.5 | 1h30 | 132 | 100 | p-propenylcumene | 94 |
| 24 | p-allylcumene | 4.4 | $RuCl_3$-β | 4.4 | 3h30 | 132 | 100 | p-propenylcumene | 88.5 |
| 25 | Methallyloxybenzene | 4 | $(C_5H_7O_2)_2Ru(CH_3—CH)_2$ | 20 | 6h | 130 | 100 | Isobutenyloxybenzene | 79 |
| 26 | Methallyloxybenzene (c) | 4 | $Ru_3(CO)_{12}$ | 20 | 4h40 | 130 | 100 | Isobutenyloxybenzene | 75 |
| 27 | p-allyloxy-bromobenzene | 5 | $(C_5H_7C_2)_3Ru$ | 25 | 6h | 130 | 92 | p-propenyloxy-bromobenzene | 82.5 |
| 28 | p-allyloxy-bromobenzene | 5 | $Ru_3(CO)_{12}$ | 5.2 | 1h50 | 130 | 92 | p-propenyloxy-bromobenzene | 82.5 |
| 29 | 1-allyl-3,4-dimethoxy-benzene | 20 | $RuBr_3$ | 8.2 | 1h | 130 | 96.2 | 1-propenyl-3,4-dimethoxybenzene | 93.5 |
| 30 | Safrole | 50 | $RuBr_3$ | 10.7 | 4h | 130 | 100 | Isosafrole | 98 |
| 31 | Safrole | 20 | $RuI_3$ | 99 | 6h50 | 130 | 73.6 | Isosafrole | 82.5 |
| 32 | N-methyl-N-allyl-aniline | 10 | $Ru_3(CO)_{12}$ | 5 | 5h30 | 130 | 82 aniline | N-methyl-N-propenyl-aniline | 60 |
| 33 | Taragon essence (mixture containing 90% of p-methoxy-allybenzene | 10 | $(C_5H_7O_2)_3Ru$ | 20 | 7h | 130 | 75 | p-methoxy-propenyl-benzene | 92.5 |
| 34 | " | 10 | $Ru_3(CO)_{12}$ | 20 | 6h30 | 130 | 91 | " | 98 |
| 35 | " | 10 | $RuCl_3$-β | 20 | 50mm | 130 | 94.5 | " | 94 |
| 36 | o-allyl-prenyloxybenzene (d) | 5 | $(C_5H_7O_2)_3Ru$ | 5 | 6h30 | 130 | 100 | o-propenyl-prenyloxy-benzene (d) | 88 |
| 37 | " | 5 | $Ru_3(CO)_{12}$ | 5.3 | 6h30 | 130 | 100 | " | 80 |
| 38 | Crude clove oil (cf. Ex. 10) | 20 | $RuBr_3$ | 49.5 | 7h15 | 130 | 90.2 | Isoeugenel | 94 |
| 39 | o-methoxy-allyloxy- | 5 | $(C_5H_7O_2)_3Ru$ | 50 | 8h | 130 | 80 | o-methoxy-propenyl-oxy | 80 |
| 40 | " | 5 | $RuCl_3$-β | 50 | 8h | 130 | 70 | " | 75 |
| 41 | " | 5 | $Ru_3(CO)_{12}$ | 10 | 8h | 130 | 100 | " | 86 | a) the radical methallyl has the formula 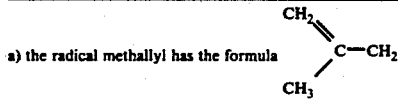

b) the radical isobutenyl has the formula 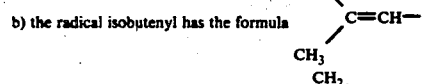

c) the radical methallyloxy has the formula 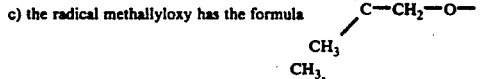

d) the radical prenyloxy has the formula 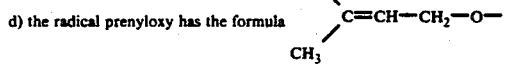

We claim:

1. A process for the isomerization of an aromatic alkenyl compound of the formula

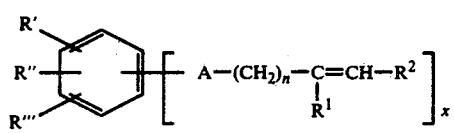

wherein R', R" and R'" are independently selected from the group consisting of hydrogen, alkyl of 1 to 5 carbon atoms, alkoxy of 1 to 5 carbon atoms, halogen, amino, hydroxy and a radical of the formula:

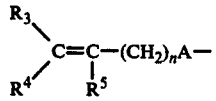

wherein $R^3$ and $R^4$ are each alkyl of 1 to 5 carbon atoms and $R^5$ is hydrogen or methyl, and two of R', R" and R''' carried by two adjacent carbon atoms of the aromatic ring can be joined together to form a —OCH₂O— radical, n is an integer from 1 to 10, A is a valence bond, an oxygen atom or an —NR⁶— group wherein R⁶ is hydrogen or alkyl of 1-5 carbon atoms, R¹ and R² are independently selected from the group consisting of hydrogen and alkyl of 1-5 carbon atoms and x is an integer from 1-3, wherein the double bond is shifted nearer to the benzene ring, said process comprising contacting the said compound with a catalyst consisting of a member selected from the group consisting of a ruthenium compound and an osmium compound at a temperature of from 40° to 200° C.

2. The process of claim 1 wherein said aromatic alkenyl compound is eugenol, methyl-eugenol, safrole, o-allylphenol, allyloxybenzene, allylbenzene, 4-phenyl-1-butene, 4-phenoxy-1-butene, p-allylcumene, methallylbenzene, methallyloxybenzene, p-allyloxybromobenzene, N-methyl-N-allyl aniline, p-methoxy-allylbenzene, o-allyl-prenyloxybenzene or o-methoxyallyloxybenzene.

3. The process of claim 1 wherein said alkenyl compound is allylbenzene, 4-phenyl-1-butene, 4-phenyl-2-butene, 5-phenyl-1-pentene, 5-phenyl-2-pentene, 1-phenyl-2-pentene, 2-methyl-4-phenyl-1-butene, 6-phenyl-1-hexene, ortho-, meta- or para-allyl toluene, p-diallylbenzene, o-, m- or p-allylphenol, 2,6-diallylphenol, 2-allyl-3,5-dimethylphenol, 2,6-diallyl-4-(2-butenyl)-phenol, 2-(3-butenyl) phenol, 2-allyl-6-ethoxyphenol, 2-methoxy-4-allylphenol, 2,6-dimethoxy-4-allylphenol, allyloxybenzene, 4-phenoxy-1-butene, 3,4-dimethoxyallylbenzene, safrole, 2,4,6-trimethoxy allylbenzene or 3-methyl-4-(2-butenyloxy) allylbenzene.

4. The process of claim 1 wherein R', R" and R''' are independently selected from the group consisting of chlorine, methyl, ethyl, propyl, butyl, amyl, methoxy, ethoxy, propoxy, butoxy, 3-methyl-2-butenyl and 3-methyl-2-butenyloxy, and R¹ and R² are independently selected from the group consisting of methyl, ethyl, propyl, butyl and amyl.

5. The process of claim 1 wherein said catalyst is a ruthenium compound.

6. The process of claim 1 wherein said catalyst is Ru(C₅H₇O₂)₃, Ru₃(CO)₁₂, (C₅H₇O₂)₂ Ru(CH₃CN)₂, [(C₅H₇O₂)₂Ru(CO)]₂, (C₅H₇O₂)₂Ru(CO) (CH₃CH₂CN), (C₅H₇O₂)₂Ru(CO) (CH₃CN), RuCl₃, OsCl₃, RuBr₃ or RuI₃.

7. The process of claim 1 wherein said catalyst is present in an amount of 0.0001 to 2% by weight, calculated as elementary ruthenium or osmium, of the compound being isomerized.

8. A process for the isomerization of an aromatic alkenyl compound of the formula

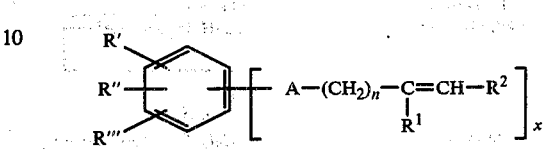

wherein R', R" and R''' are independently selected from the group consisting of hydrogen, alkyl containing 1-5 carbon atoms, alkoxy containing 1-5 carbon atoms, halogen, amino, hydroxy and a radical of the formula

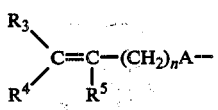

wherein R³ and R⁴ are each alkyl containing 1-5 carbon atoms and R⁵ is hydrogen or methyl, and two of R', R" and R''' carried by two adjacent carbon atoms of the aromatic ring can be joined together to form a —OCH₂O— radical, n is an integer of 1-10, A is a valence bond, an oxygen atom or an —NR⁶— group wherein R⁶ is hydrogen or alkyl containing 1-5 carbon atoms, R¹ and R² are independently selected from the group consisting of hydrogen and alkyl containing 1-5 carbon atoms and x is an integer of 1-3, wherein the double bond is shifted nearer to the benzene ring, said process consisting essentially of contacting said compound with a catalyst consisting of a member selected from the group consisting of Ru(C₅H₇O₂)₃, Ru₃(CO)₁₂, (C₅H₇O₂)₂Ru(CH₃CN)₂, [(C₅H₇O₂)₂Ru(CO)]₂, (C₅H₇O₂)₂Ru(CO) (CH₃CH₂CN), (C₅H₇O₂)₂Ru(CO) (CH₃CN), RuCl₃, OsCl₃, RuBr₃ and RuI₃, at a temperature of from 40° to 200° C., said catalyst being present in an amount of 0.0001 to 2% by weight, calculated as elementary ruthenium or osmium, respectively, of said aromatic alkenyl compound being isomerized.

* * * * *